United States Patent [19]

Frank et al.

[11] 4,278,811

[45] Jul. 14, 1981

[54] PROCESS FOR THE PREPARATION OF TRIS(AMINOMETHYL)PHOSPHINE OXIDE AND ITS TERNARY SALTS

[75] Inventors: Arlen W. Frank, Slidell; Donald J. Daigle, New Orleans; Russell M. H. Kullman, Harahan, all of La.

[73] Assignee: The United States of America as represented by the Secretary of Agriculture, Washington, D.C.

[21] Appl. No.: 128,440

[22] Filed: Mar. 10, 1980

Related U.S. Application Data

[63] Continuation-in-part of Ser. No. 964,854, Nov. 29, 1978, Pat. No. 4,196,149.

[51] Int. Cl.$^3$ .............................................. C07F 9/53
[52] U.S. Cl. .................................................. 564/15
[58] Field of Search ........................ 260/551 P, 583 E

[56] References Cited

FOREIGN PATENT DOCUMENTS

289093 12/1969 U.S.S.R. ................................ 260/551 P

OTHER PUBLICATIONS

Trostyenskaya et al., CA 68:13084j, (1968).

*Primary Examiner*—Thomas A. Waltz
*Attorney, Agent, or Firm*—M. Howard Silverstein; Raymond C. Von Bodungen; David G. McConnell

[57] ABSTRACT

Tris(aminomethyl)phosphine oxide and its ternary salts, useful as catalysts for the chemical finishing of cotton, are prepared by the hydrolysis of tris(N-carbalkoxylaminomethyl)-phosphine oxides having the formula $(RO_2CNHCH_2)_3PO$ with an alkali or alkaline earth in the presence of water, followed optionally by acidification.

4 Claims, No Drawings

PROCESS FOR THE PREPARATION OF TRIS(AMINOMETHYL)PHOSPHINE OXIDE AND ITS TERNARY SALTS

This is a continuation-in-part of Ser. No. 964,854, now U.S. Pat. No. 4,196,149, "Ternary Salts of Tris-(aminomethyl)phosphines and their Oxides", by Arlen W. Frank, Donald J. Daigle, and Russell M. H. Kullman, filed Nov. 29, 1978.

CROSS REFERENCES TO RELATED APPLICATIONS

Ser. No. 964,852: "Tris(N-carbalkoxylaminomethyl)-phosphine Oxides and Sulfides", by Arlen W. Frank, filed Nov. 29, 1978.

Ser. No. 61,322: "Ternary Salts of Tris(aminomethyl)-phosphine Oxide prepared by Acid Hydrolysis of its N-Carbalkoxyl Derivatives", by Arlen W. Frank, Donald J. Daigle, and Russell M. H. Kullman, filed July 19, 1979.

BACKGROUND OF THE INVENTION (1) Field of the Invention

This invention relates to a process for the preparation of tris(aminomethyl)phosphine oxide and its ternary salts. More particularly, it relates to a process for hydrolyzing tris(N-carbalkoxylaminomethyl)phosphine oxides to tris(aminomethyl)phosphine oxide under alkaline conditions, whereby the product may be isolated directly or converted to one of its ternary salts.

(2) Description of the Prior Art

Tris(aminomethyl)phosphine oxide, $(NH_2CH_2)_3PO$, has hitherto been accessible only through the Gabriel synthesis from tris(chloromethyl)phosphine oxide, $(ClCH_2)_3PO$ [Trostyanskaya et al., J. Gen Chem. USSR 37, 1572-74 (1967); Chem. Abstr. 68, 13084 (1968)]. In Ser. No. 964,854, we described some novel ternary salts of tris(aminomethyl)phosphine oxide having the formula $(NH_3^+CH_2)_3PO\ 3X^-$, and in Ser. No. 61,322 we described how such ternary salts can be prepared from tris(N-carbalkoxylaminomethyl)phosphine oxides, $(RO_2CNHCH_2)_3PO$, by hydrolysis with acids. The carbamate groups are difficult to cleave with any but the strongest acids, i.e. those having the formula HX, where X=halogen. A better method was needed to make this hydrolysis useful for preparing larger quantities of tris(aminomethyl)phosphine oxide.

SUMMARY OF THE INVENTION

This invention relates to a process for the preparation of tris(aminomethyl)phosphine oxide and its ternary salts which cmprises hydrolyzing a tris(N-carbalkoxylaminomethyl)phosphine oxide having the formula $(RO_2CNHCH_2)_3PO$, where R is an alkyl radical having from 1 to 6 carbon atoms, with an alkali or alkaline earth in the presence of water, and recovering the product therefrom either in the form of the free base or a ternary salt thereof.

The principal object of the invention is to develop an improved process for preparing tris(aminomethyl)phosphine oxide and its ternary salts. Another object is to develop a process that yields tris(aminomethyl)phosphine oxide directly. Further objects will be apparent from the following detailed description of the preferred embodiments of the invention.

DESCRIPTION OF THE PREFERRED EMBODIMENTS

The hydrolysis of a tris(N-carbalkoxylaminomethyl)-phosphine oxide with an alkali or alkaline earth is exemplified by the following equation, using barium hydroxide for the purpose of illustration:

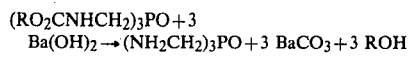

The tris(N-carbalkoxylaminomethyl)phosphine oxides needed for the purposes of this invention are described in a paper by Frank and Drake, J. Org. Chem. 42, 4040-45 (1977). The nature of the R group is immaterial because it is cleaved off in the hydrolysis and removed as ROH. However, for practical purposes it is preferable to employ substances in which R is an alkyl radical having from 1 to 6 carbon atoms, such as methyl, ethyl, isopropyl, 2-methoxyethyl, n-butyl, and the like.

By alkali and alkaline earth is meant any of the Group 1a metals—lithium, sodium, potassium, rubidium, and cesium—or Group 2a metals—magnesium, calcium, strontium, and barium—in the form that these metals take when dissolved in water, i.e. oxides, hydroxides, and mixtures thereof. Typical reagents used in the practice of this invention are sodium hydroxide, barium hydroxide, and calcium oxide or their commercial equivalents caustic soda, baryta, and lime. The alkaline earths are preferred because they form highly insoluble carbonates that are easily removed.

The molar ratio of alkali or alkaline earth to tris(N-carbalkoxylaminomethyl)phosphine oxide should be approximately 3:1, in conformity with the stoichiometry of the equation above. If it is less than 3:1, the hydrolysis will be incomplete. Ratios higher than 3:1 can be tolerated, for it was found that the product, tris-(aminomethyl)phosphine oxide, is unaffected by prolonged boiling with an excess of the reagent (see Example 5). In fact, a slight excess over the 3:1 ratio is preferred in order to ensure complete hydrolysis. The excess reagent can be subsequently destroyed by acidification (see Examples 1 and 2), by carbonation (see Examples 3-5), or by any other suitable means.

The molar ratio needed for complete hydrolysis is the same for alkali as for alkaline earth. With alkali, the carbon dioxide cleaved off in the hydrolysis is trapped either as carbonate or bicarbonate, depending on the molar ratio used. For example, if the alkali is sodium hydroxide, the carbon dioxide is trapped as sodium bicarbonate $(NaHCO_3)$ if the molar ratio is 3:1, and as sodium carbonate $(Na_2CO_3)$ if the molar ratio is 6:1.

The hydrolysis can be carried out at temperatures ranging from 50° C. to 150° C., and at pressures of 0.5 to 1.5 atmospheres. It is convenient to carry out the hydrolysis at or near the boiling point of water, and at about atmospheric pressure. If the alcohol liberated in the reaction has a lower boiling point than water, it is expedient to distil the vapors at a slow rate and replace the loss with water; to prevent a buildup of alcohol which would depress the boiling point and slow down the hydrolysis (see Example 5).

The tris(aminomethyl)phosphine oxide may be isolated from the hydrolysis mixture by any suitable means. If the reagent is an alkali, the product may be isolated by acidification of the reaction mixture, as illustrated in Examples 1 and 2. Separation of the salts may present a problem, as shown in Example 1. If the reagent is an alkaline earth, the problem can be avoided because the reagent consumed in the hydrolysis and any excess reagent present can both be removed as the insoluble carbonate, as illustrated in Examples 3–5. The product can be isolated as a crystalline ternary salt such as the trihydrochloride (Example 3) or the bis(dihydrogen sulfate) (Example 4). It may also be isolated directly (Example 5), but in this case the product is found to be contaminated with a by-product identified as 5-aminomethyl-1,3-diaza-5-phosphorinan-2,5-dione:

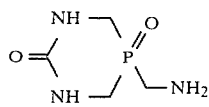

This by-product is a white, crystalline solid, mp 204°–206° C., that forms crystalline 1:1 salts with acids. The yield of the by-product is highest (15–20%) in preparative-scale reactions. We suggest, without wishing to be bound by any specific hypothesis, that the by-product is formed during the hydrolysis by degradation of a carbalkoxyamino group to an isocyanate group ($-NHCO_2R \rightarrow -NCO + ROH$), followed by ring closure with an adjacent amino group.

Tris(aminomethyl)phosphine oxide, as normally isolated, is a colorless oil that analyses as a hydrate (Example 4). The product can be dehydrated by drying at 100° C. (Example 4) or by azeotropic distillation with benzene (Example 5), but remains an oil, $n_D^{20} 1.5682$. The refractive index falls rapidly when the oil is exposed to the air. The product has none of the properties ascribed to it in the literature; the compound described by Trostyanskaya et al (loc. cit.) was a white, hygroscopic solid, mp 40° C. after sublimation or recrystallization from dimethylformamide, that formed only a monohydrochloride, mp above 320° C., upon treatment with HCl.

Hydrolysis of related compounds having the following structures,
$(RO_2CNHCH_2)_4P^+X^-$
$(RO_2CNHCH_2)_3P$
$(RO_2CNHCH_2)_3PS$
where R is as defined above and X is CL or $SO_4/2$ does not give the expected products, nor is there any evidence of the alkyl-nitrogen fission that occurs when these compounds are hydrolyzed with acid. Hydrolysis of the quaternary phosphonium salts or the tertiary phosphines with barium hydroxide under the conditions defined above gives tris(aminomethyl)phosphine oxide, isolated as the trihydrochloride, in 75 to 78% yield, even though air is excluded and the excess reagent is destroyed with carbon dioxide from a cylinder instead of Dry Ice. Hydrolysis of the tertiary phosphine sulfide with barium hydroxide under the same conditions is complete after two hours, but the product is a mixture of unidentified amine salts.

The ternary salts of tris(aminomethyl)phosphine oxide are, as disclosed and amply documented in Ser. No. 964,854, useful as catalysts for the chemical reactions employed in the finishing of cotton with methylol amide crosslinking agents. These agents are used extensively in the textile industry to impart wrinkle resistance and durable press properties to cotton and cotton blend fabrics.

The following examples are given to illustrate the preparation of tris(aminomethyl)phosphine oxide and its ternary salts, and should not be construed as limiting the scope of the invention. Melting points were corrected. Infrared (IR) spectra were taken on a Perkin-Elmer 137B (m=medium, s=strong, vs=very strong, br=broad). Nuclear magnetic resonance (NMR) spectra were taken on a Varian EM-360L with DSS as an internal lock ($^1H$ spectra), or a Varian CFT-20 with dioxane as an internal reference ($^{13}C$ spectra). Elemental analyses were performed by Galbraith Laboratories, Inc., Knoxville, Tenn.

EXAMPLE 1

A slurry of 15.56 g (0.05 mol) of tris(N-carbomethoxylaminomethyl)phosphine oxide, 8.00 g (0.20 mol) of sodium hydroxide, and 100 ml of water was heated to reflux under an argon atmosphere, and held at reflux for 5 hr. The solids dissolved, but no gassing was noted. After cooling, the solution was acidified cautiously with 6 N HCl (strong effervescence), boiled briefly to expel the $CO_2$, and stripped under reduced pressure. The residue, a semi-solid mass, was shaken with ethanol and filtered, giving 20.94 g of white, crystalline solid, dec. 226° C. (reddening), identified by mp, IR, and $^1H$ NMR as a mixture of tris(aminomethyl)phosphine oxide trihydrochloride (9.25 g, 75.0% yield) and sodium chloride (11.69 g, 0.40 mol).

The salts are difficult to separate because of their similar solubility characteristics.

EXAMPLE 2

Hydrolysis was carried out as in Example 1, but after acidification and expulsion of the $CO_2$ the semisolid mass was neutralized to pH 9.0 with sodium hydroxide, stripped under reduced pressure, shaken with ethanol and filtered, giving 6.34 g of a colorless oil identified as tris(aminomethyl)phosphine oxide hydrate (81.7% yield) by comparison of its IR spectrum with that of Example 4.

EXAMPLE 3

A slurry of 15.56 g (0.05 mol) of tris(N-carbomethoxylaminomethyl)phosphine oxide, 47.32 g (0.15 mol) of barium hydroxide octahydrate, and 150 ml of water was heated to reflux with constant stirring, and held at reflux for 2 hr. Solids were formed as the reagents dissolved, but no gassing occurred. After cooling, the mixture was filtered, giving 30.36 g (0.15 mol) of white solid identified by IR as barium carbonate. The filtrate was gassed with carbon dioxide from a Dry Ice generator, boiled briefly, and filtered again to remove any excess base that might be present. None separated. The filtrate, now neutral, was stripped and acidified with 100 ml of 6 N HCl (no gassing), giving 11.49 g (93.2% yield) of tris(aminomethyl)phosphine oxide trihydrochloride as a white, crystalline solid, dec. 227°–28° C. (reddening), identical (IR, $^1H$ NMR) to the product of Example 1.

EXAMPLE 4 hydrolysis was carried out as in Example 3, but the neutral filtrate was acidified with 96% sulfuric acid (15.33 g, 0.15 mol) instead of hydrochloric acid. The product was collected on a filter, rinsed with ethanol and dried, giving 15.05 g (90.3% yield) of tris(aminomethyl)phosphine oxide bis(dihydrogen sulfate), $(NH_2CH_2)_3PO.2H_2SO_4$ as a white, crystalline solid, dec. 224° C. after recrystallization from water (7 ml/g).

Anal. Calcd. for $C_3H_{16}N_3O_9PS_2$: C, 10.81; H, 4.84; N, 12.61; P, 9.29; S, 19.24. Found: C, 10.82; H, 4.97; N, 12.58; P, 9.40; S, 19.02.

Its IR spectrum in Nujol showed absorption peaks at 820 m, 1100 s, 1180 vs (P=O), 1600 m ($NH_3^+$), and 2600–2700 m ($NH_3^+$) $cm^{-1}$. The $^1$H NMR spectrum in $D_2O$ showed a doublet for the three methylene groups at $\delta 3.92$ ppm (J=5.7 Hz). The salt is an anhydrous, non-hydroscopic substance that is insoluble in organic solvents and only slightly soluble in water.

A hot solution of 31.55 g (0.1 mol) of barium hydroxide octahydrate in 250 ml of water was added to a hot solution of 13.33 g (0.04 mol) of the above salt in 250 ml of water. Solids separated at once. After 1 hour at 65° C., the excess base was destroyed by passing a stream of carbon dioxide from a Dry Ice generator under the surface of the mixture until the contents were neutral. The mixture was heated to boiling, filtered through Celite filter aid and stripped under vacuum, giving 6.20 g (100% yield) of tris(aminomethyl)phosphine oxide hydrate, $(NH_2CH_2)_3PO \cdot H_2O$ as a colorless oil, $n_D^{20}$ 1.5538.

Anal. Calcd. for $C_3H_{14}N_3O_2P$: C, 23,22; H, 9.10; N, 27.09; P, 19.96. Found: C, 23.47; H, 9.16; N, 27.12; P, 20.30.

Its IR spectrum (neat) showed absorption bands at 830 s, br, 11140 vs (P=O), 1580 m (NH), and 3300 vs (NH) $cm^{-1}$. The $^1$H NMR spectrum in $D_2O$ showed a doublet for the three methylene groups at $\delta 3.22$ ppm (J=6.0 Hz). The product is a colorless, hygroscopic oil, soluble in water and the lower alcohols but insoluble in other organic solvents. A portion of the product, dried in a drying pistol at 100° C., had a refractive index ($n_D^{20}$) of 1.5684.

EXAMPLE 5

A slurry of 311.2 g (1 mol) of tris(N-carbomethoxylaminomethyl)phosphine oxide, 237.1 g (3.2 mols) of calcium hydroxide, and 2500 ml of water was heated to reflux in an apparatus fitted with a mechanical stirrer and a K-head reflux condenser. Some of the methanol-containing distillate was drawn off from time to time and replaced by sufficient water to maintain the original volume. After 5 hr at 98° C., the mixture was carbonated with Dry Ice until neutral by means of a tube extending through the reflux condenser and under the surface. It was then purged with argon to prevent the carbon dioxide from being reabsorbed upon cooling, and allowed to cool. Next day, the mixture was filtered, removing 323.5 g (101.0%) of calcium carbonate, and stripped under reduced pressure. After drying, the residue was shaken with ethanol and filtered, giving 23.9 g (14.6% yield) of the by-product 5-aminomethyl-1,3-diaza-5-phosphorinan-2,5-dione,

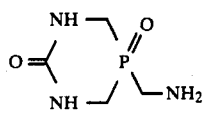

as a white, crystalline solid, mp 198°–200° C. A portion of this substance recrystallized from ethanol-water had mp 204°–206° C.

Anal. Calcd. for $C_4H_{10}N_3O_2P$: C, 29.45; H, 6.18; N, 25.77; P, 18.99; MW, 163.12. Found: C, 29.13; H, 6.30; N, 25.99; P, 18.99; MW 162.

The IR spectrum of the by-product in Nujol showed absorption peaks at 760–780 s, 927 m, 1155 vs (P=O), 1235 s, 1290 m, 1410 m, 1520 s (NH, amide II), 1640 m, 1670 vs (C=O, amide I), 2900 m, 3100 s, and 3270 vs (NH) $cm^{-1}$. The $^1$H NMR spectrum in $D_2O$ showed a doublet for the chain $CH_2$ group at $\delta 3.37$ ppm (J=5.5 Hz), a triplet for one of the ring $CH_2$ groups at $\delta 3.62$ ppm (J=1.5 Hz), and a singlet for the other ring $CH_2$ group at $\delta 3.82$ ppm in a ratio of 2:2:2. The by-product is soluble in water and insoluble in organic solvents. After 5 hr refluxing with calcium hydroxide in water, most of it (86.9%) was recovered unchanged.

The by-product forms crystalline 1:1 salts with acids. A solution of 4.89 g (0.03 mol) of the by-product in 15 ml of water was treated with 25 ml of conc. hydrochloric acid, stripped under vacuum, shaken with ethanol and filtered, giving 5.39 g (90.0% yield) of 5-aminomethyl-1,3-diaza-5-phosphorinan-2,5-dione hydrochloride

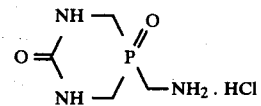

as a white, crystalline solid, dec. 244° C.

Anal. Calcd. for $C_4H_{11}ClN_3O_2P$: C, 24.07; H, 5.56; Cl, 17.77; N, 21.06; P, 15.52. Found: C, 24.04; H, 5.66; Cl, 17.95; N, 20.83; P, 15.56.

Its IR spectrum in Nujol showed absorption peaks at 746 m, 834 m, 935 m, 1075 m, 1115 m, 1175 vs (P=O), 1240 s, 1510 vs (NH, amide II), 1600 s, 1650 vs (C=O, amide I), and 3130 vs (NH) $cm^{-1}$. The $^1$H NMR spectrum in $D_2O$ showed a doublet for the chain methylene group at $\delta 3.85$ ppm (J=7.5 Hz) and a doublet for the two ring methylene groups at $\delta 3.92$ ppm (J=12.0 Hz) in a ratio of 2:4.

The dihydrogen sulfate

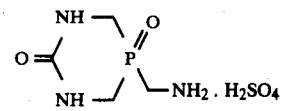

was similarly prepared as a white, crystalline solid, dec 237° C., from the by-product and conc. Sulfuric acid in 98.8% yield. Its IR spectrum in Nujol showed absorption peaks at 862 m, 1040 s, 1170 s (P=O), 1240 m, 1495 s, (NH, amide II), 1650 s (C=O, amide I), and 3200 s (NH) $cm^{-1}$. The $^1$H NMR spectrum in $D_2O$ showed a doublet for the chain methylene group at $\delta 3.85$ ppm (J=7.5 Hz), and a doublet for the two methylene groups at $\delta 3.92$ ppm (J=12.0 Hz) in a ratio of 2:4.

The salts of the by-product are soluble in water and insoluble in organic solvents. Unlike the salts of tris-(aminomethyl)phosphine oxide, they are also soluble in conc. HCl and $H_2SO_4$, respectively. Neutralization of the salts with a base such as sodium hydroxide or calcium hydroxide regenerates the by-product quantitatively.

The filtrate from which the by-product was separated was stripped under reduced pressure, giving 116.0 g (74.8% yield) of the main product, tris(aminomethyl)phosphine oxide hydrate, $(NH_2CH_2)_3PO \cdot H_2O$, as a colorless oil, $n_D^{20}$ 1.5655, identical (IR, $^1H$ NMR) to the product of Example 4. The $^{13}C$ NMR spectrum of the hydrate in $D_2O$ showed one signal for the three methylene carbons at $\delta 35.7$ ppm, split into a doublet of triplets owing to coupling with phosphorus (1:1, J=66.9 Hz) and hydrogen (1:2:1, J=137.0 Hz).

A portion of the product, dried by azeotropic distillation with benzene using an efficient stirrer, oil bath, and Dean-Stark trap to collect the water had a refractive index ($n_D^{20}$) of 1.5682. Another portion of the product was recovered unchanged after 5 hr refluxing with calcium hydroxide in water. Another portion of the product was treated with conc. hydrochloric acid, giving the crystalline trihydrochloride, dec. 232°—33° C. (reddening, identical (IR, $^1H$ NMR) to the product of Example 1. The $^{13}C$ NMR spectrum of the salt in $D_2O$ showed one signal for the three methylene carbons at $\delta 36.8$ ppm, split into a doublet of triplets owing to coupling with phosphorus (1:1, J=71.4 Hz) and hydrogen (1:2:1, J=144.8 Hz).

I claim:

1. A process for preparing tris(aminomethyl)phosphine oxide which comprises (a) mixing a tris(carbalkoxylaminomethyl)phosphine oxide having the formula $(RO_2CNHCH_2)_3PO$, where R is an alkyl radical having from 1 to 6 carbon atoms, with a reagent selected from the group consisting of alkalis and alkaline earths, in the presence of water, (b) heating the mixture at a temperature of about 100° C. until all three of the acyl-nitrogen bonds are cleaved, (c) destroying the excess reagent with carbon dioxide at a temperature of about 100° C., and (d) recovering the product from the resulting reaction mixture.

2. The process of claim 1, wherein the reagent is sodium hydroxide.

3. The process of claim 1, wherein the reagent is an alkaline earth selected from calcium hydroxide and barium hydroxide.

4. The process of claim 1, wherein the product is recovered in the form of ternary salt after acidification.

* * * * *